United States Patent [19]
Glover et al.

[11] Patent Number: 4,890,479
[45] Date of Patent: Jan. 2, 1990

[54] SYSTEM AND METHOD FOR MONITORING WET BULB TEMPERATURE IN A FLUE GAS STREAM

[75] Inventors: Robert L. Glover, Lockport, N.Y.; Verle V. Bland, Evergreen, Colo.

[73] Assignee: Electric Power Research Institute, Inc., Palo Alto, Calif.

[21] Appl. No.: 310,268

[22] Filed: Feb. 13, 1989

Related U.S. Application Data

[63] Continuation-in-part of Ser. No. 5,109, Jan. 20, 1987, Pat. No. 4,809,537.

[51] Int. Cl.$^4$ .............................................. G01N 31/00
[52] U.S. Cl. ........................................ 73/29; 73/338; 236/44 A
[58] Field of Search ............... 236/44 R, 44 A; 34/50; 73/338, 29, 336.5, 77; 165/21; 374/54

[56] References Cited

U.S. PATENT DOCUMENTS

| | | | |
|---|---|---|---|
| 3,603,135 | 9/1971 | Kawaguchi | 73/77 |
| 3,712,140 | 3/1971 | Grasso et al. | 73/338 |
| 3,890,828 | 6/1975 | Pleva | 73/29 |
| 4,129,250 | 12/1978 | Chikin | 73/77 |
| 4,461,167 | 7/1984 | Kent et al. | 73/29 |

Primary Examiner—William E. Wayner
Attorney, Agent, or Firm—Flehr, Hohbach, Test, Albritton & Herbert

[57] ABSTRACT

System and method for continuously monitoring the wet bulb temperature in a flue gas stream, for example, at the inlet of a spray dryer. A sample of the flue gas is maintained at substantially the same moisture content and temperature as the gas in the flue. The temperature of this sample is measured with a sensor surrounded by a liquid absorbent wick which is immersed in liquid maintained at a substantially constant level.

13 Claims, 3 Drawing Sheets

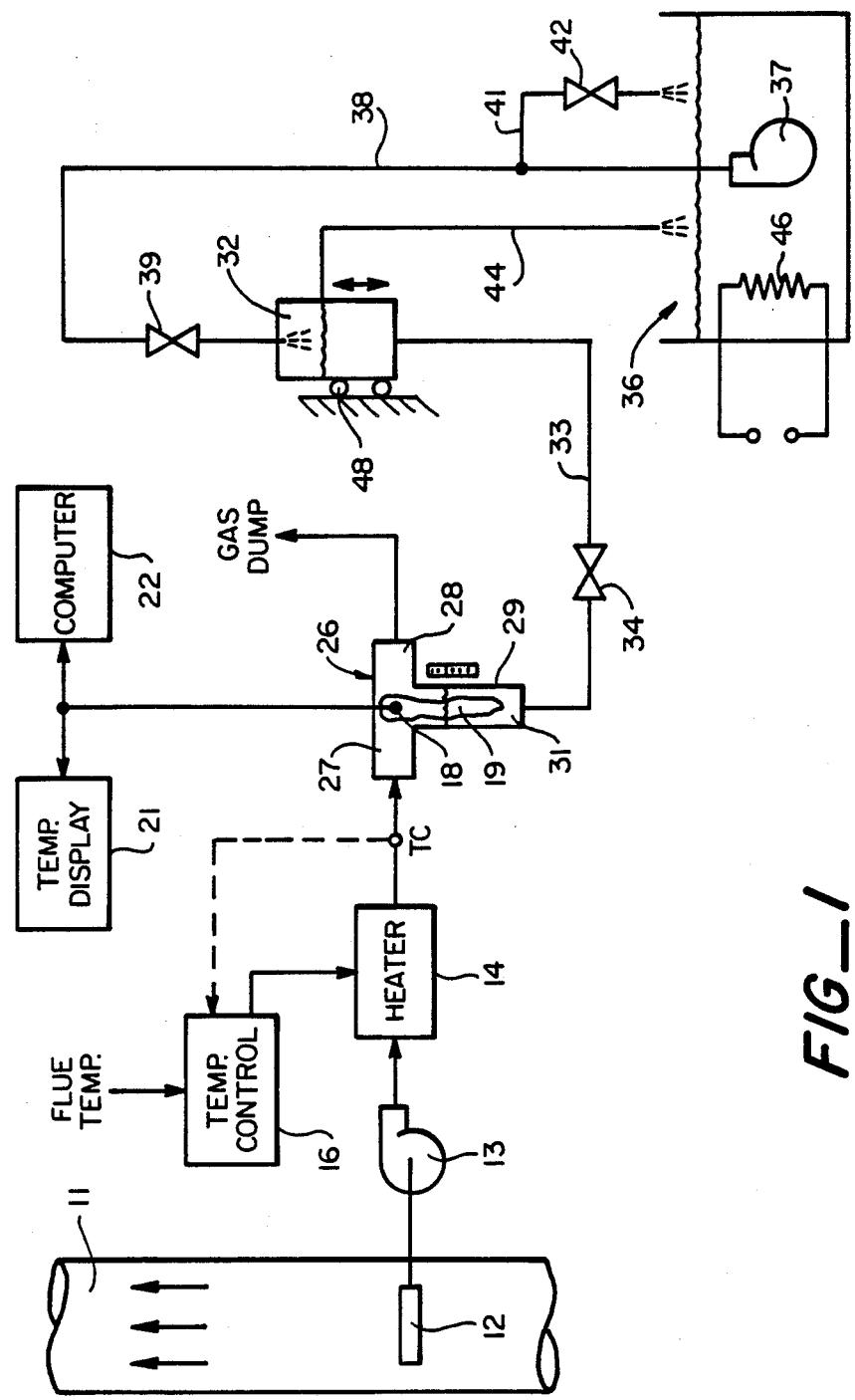
FIG_1

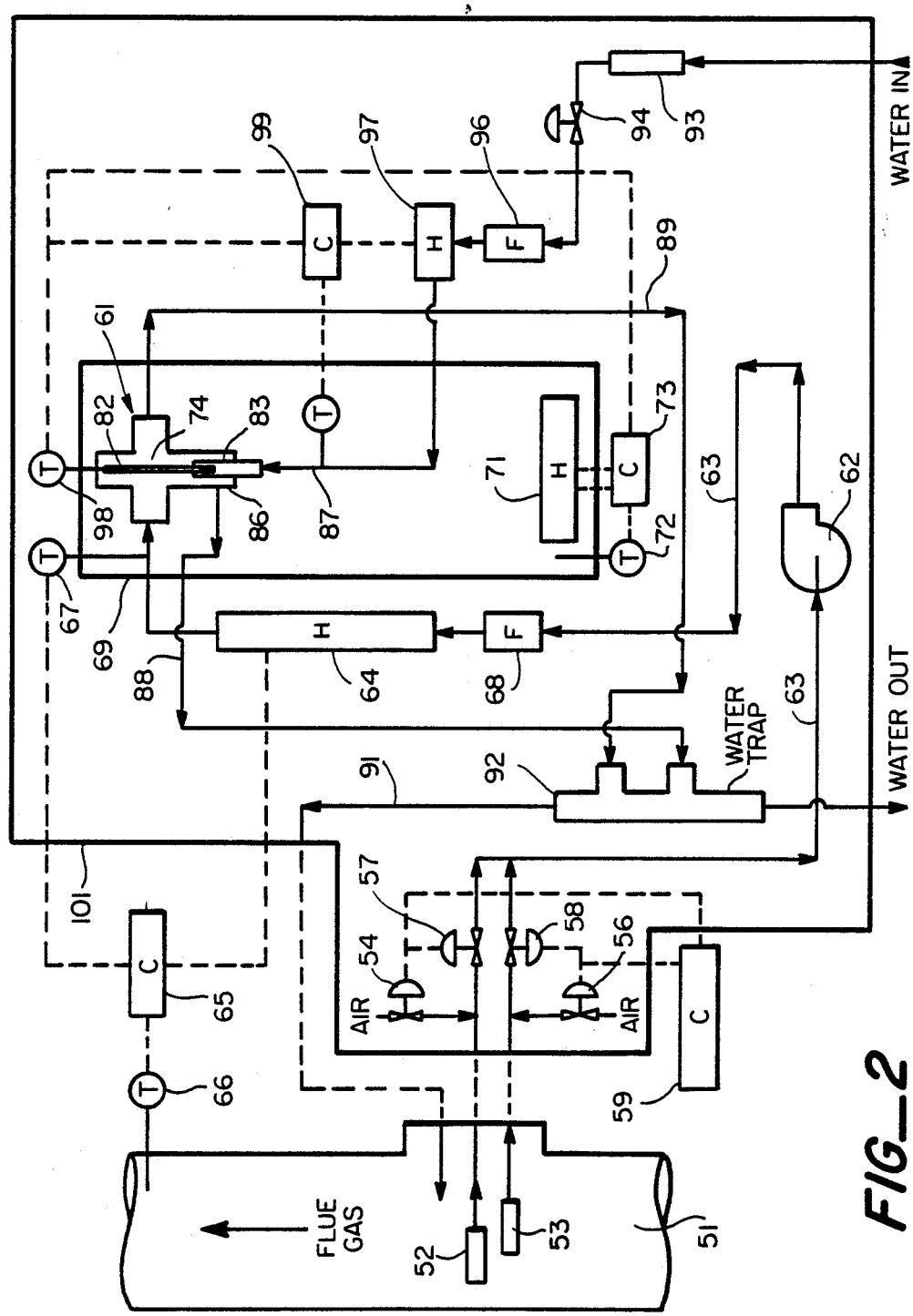
FIG_2

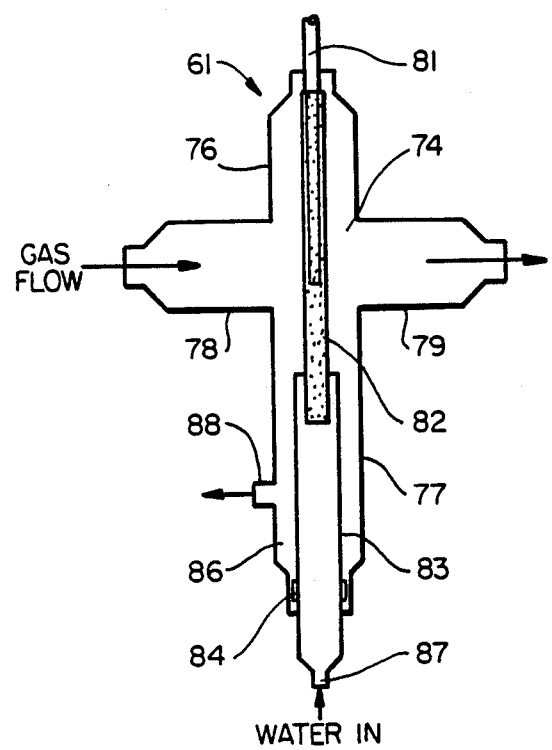
FIG_3
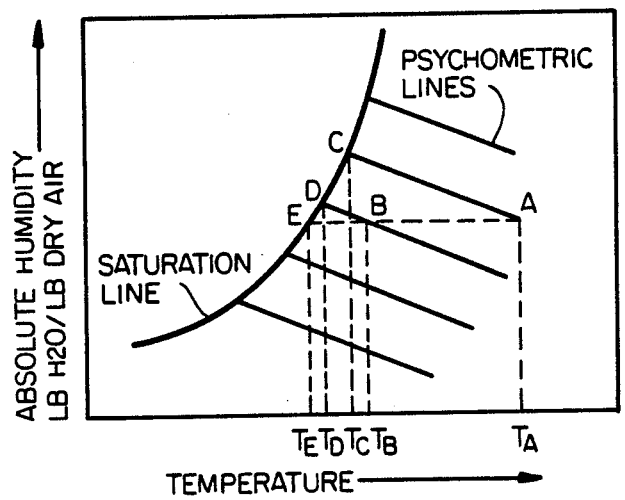
FIG_4

SYSTEM AND METHOD FOR MONITORING WET BULB TEMPERATURE IN A FLUE GAS STREAM

This is a continuation-in-part of Ser. No. 07/005,109, filed Jan. 20, 1987.

This invention pertains generally to temperature measurement, and more particularly to a system and method for monitoring the wet bulb temperature in a flue gas stream as found, for example, at the inlet to a spray dryer.

Spray dryers are employed in electric power generating plants to remove $SO_2$ and other contaminants from the exhaust gases of coal fired boilers. In order to operate the spray dryers in their most efficient range, the wet bulb temperature of the incoming gas must be monitored closely.

In the past, the wet bulb temperature at the inlet to spray dryers has been monitored manually. This technique is costly from a labor standpoint, and it has the further disadvantage of not permitting the gas stream temperature to be monitored on a continuous basis. Continuous monitoring is desirable because it permits better control over the spray dryer approach to saturation (outlet temperature minus wet bulb temperature) and more efficient operation of the dryer.

U.S. Pat. No. 4,129,250 discloses a system which is intended for use in the continuous measurement and control of the relative humidity of exhaust gas from industrial dryers. This system employs both wet and dry bulb sensors, with means for periodically dipping the wet bulb sensor into a container of water. A voltage developed from the sensors provides a measure of the relative humidity and is utilized to control the amount of air discharged from the dryer to the atmosphere. After each dipping of the sensor, the application of the control voltage must be delayed until the wet bulb sensor reaches equilibrium with the exhaust gas. Variations in the wetness of the sensor can also affect the temperature and humidity readings. While this system may provide some measure of automated control over the relative humidity of the exhaust gas, it does have certain limitations and disadvantages, and it does not provide a continuous readout of the wet bulb temperature which is needed to efficiently control the spray dryer operation.

It is in general an object of the invention to provide a new and improved system and method for monitoring the wet bulb temperature in a flue gas stream.

Another object of the invention is to provide a system and method of the above character which overcome the limitations and disadvantages of systems and methods heretofore provided for measuring wet bulb temperature.

These and other objects are achieved in accordance with the invention by extracting a sample of the flue gas, filtering the sample, heating the filtered sample to maintain it at substantially the same temperature as the gas in the flue, measuring the temperature of the heated sample with a sensor surrounded by a liquid absorbent wick, applying liquid to the wick from a reservoir, and maintaining the liquid in the reservoir at a substantially constant level. Liquid is supplied to the reservoir from a second reservoir, with the level of the liquid in the first reservoir being dependent upon the level of the liquid in the second reservoir. Liquid is supplied continuously to the second reservoir to maintain it in an overflow condition, and this maintains the liquid at substantially constant levels in both the first reservoir and the second reservoir.

FIG. 1 is a schematic diagram of one embodiment of a system for monitoring the wet bulb temperature of a flue gas stream in accordance with the invention.

FIG. 2 is a schematic diagram of one embodiment of a system for monitoring the wet bulb temperature of a flue gas stream in accordance with the invention.

FIG. 3 is a cross sectional view, somewhat schematic, of a wet bulb tee assembly utilized in the embodiment of FIG. 2.

FIG. 4 is a simplified psychometric chart for a wet bulb temperature monitor according to the invention.

In FIG. 1, the invention is illustrated in connection with a flue 11 at the inlet to a spray dryer (not shown) for cleaning the exhaust gas of a boiler at an electric power generating station.

Means is provided for continuously extracting a sample from the gas stream in the flue. This means includes a filter 12 mounted within the flue and a pump 13 which draws the sample through the filter. In one presently preferred embodiment, the filter comprises a sintered, stainless steel filter, and the pump comprises an insulated diaphragm pump. The filter serves to remove solid contaminants such as fly ash from the gas sample.

The filtered gas sample is pumped to a heater 14 where it is reheated to substantially the same temperature as the gas in the flue. In a preferred embodiment, the heater comprises a low voltage nichrome heater. A temperature control 16 monitors the temperature of the gas in the flue and at the output of the heater and controls the operation of the heater to make the output temperature equal to the flue temperature.

The wet bulb temperature of the reheated gas sample is measured by a thermocouple sensor 18 surrounded by a liquid absorbent wick 19. The temperature measured by the sensor is displayed by a thermocouple signal processing and display unit 21 connected to the sensor, and data from the sensor is also supplied to a computer 22 in a data acquisition system. Sensor 18 and wick 19 are mounted in a T-shaped vessel 26 having a pair of horizontally extending arms 27, 28 and a depending arm or reservoir 29. The gas sample is introduced into the T-shaped vessel through arm 27 and exhausted through arm 28, and wick 19 extends into reservoir 29 where it is immersed in a suitable liquid 31 such as water. Liquid absorbed by the wick wets the thermocouple sensor to provide the desired wet bulb reading.

Means is provided for maintaining the liquid in reservoir 29 at a substantially constant level. This is important from the standpoint of accurate temperature readings. If the level is too low, insufficient liquid will be supplied to the sensor. If the level is too high, the wick will be overwetted. In either instance, the temperature reading will be inaccurate.

The means for maintaining the substantially constant liquid level includes a second reservoir 32 which is connected in fluid communication with reservoir 29 by a line 33 which extends between the lower portions of the two reservoirs. A flow control valve 34 is provided in line 33. Water is supplied to reservoir 32 from a tank 36 by a pump 37 and a line 38. A flow control valve 39 in line 38 controls the rate at which the water is delivered to reservoir 32. A by-pass line 41 having a flow control valve 42 is connected to line 38 for returning excess water from pump 37 to tank 36. An overflow line 44 is connected to reservoir 32 for returning water above a predetermined level in this reservoir to tank 36.

By maintaining reservoir 32 continuously in an overflow condition, the water in this reservoir is maintained at a substantially constant level, the overflow level.

A heater 46 is provided for heating the water in tank 36 and, hence, the water applied to sensor 18.

The level of the water in reservoir 29 is dependent upon the level of the water in reservoir 32 and the relative pressures above the water in reservoirs 32 and 29. The level in reservoir 29 can be changed by raising or lowering reservoir 32 and by adjusting the rate at which water is delivered to this reservoir. Reservoir 32 is mounted on an adjustable mount 48, and coarse adjustments of the water level are made by means of this mount. Finer adjustments are made by means of inlet valve 39, and small changes in the rate of water flow into reservoir 32 will result in small changes in static head at the overflow point. These water level adjustments are made on a periodic basis to compensate for static pressure differences in the flue, and hence in the gas sample, due to boiler load variations.

Operation and use of the monitoring system, and therein the method of the invention, are as follows. A gas sample is extracted from the flue through filter 12 and reheated by heater 14 to substantially the same temperature as the gas in the flue. The wet bulb temperature of the reheated gas sample is monitored by sensor 18 and displayed.

As the water in reservoir in 29 is consumed by the wicking action and by evaporation at the wet bulb sensor, it is replenished from reservoir 32. Water is supplied to reservoir 32 from tank 36 at a rate which is sufficient to maintain reservoir 32 in an overflow condition. As long as reservoir 32 is in an overflow condition, the water level in this reservoir is substantially constant, and this keeps the water level in reservoir 29 substantially constant. The water level in reservoir 29 can be adjusted by raising or lowering reservoir 32 or by increasing or decreasing the rate of flow into reservoir 32.

In the embodiment of FIG. 2, the invention is illustrated in connection with a dryer flue gas duct 51 similar to flue 11. A gas sample is removed from the duct through a pair of sintered filters 52, 53, each of which is similar to filter 12. Pressurized air is supplied to the filters through valves 54, 56 to remove particulate matter from the surfaces of the filters. Valves 57, 58 permit the filters to be selectively isolated from the remainder of the system for purging. In operation, these valves are opened alternately so that the sample passes through one of the filters while the other is being purged. A controller 59 sequences the opening and closing of the valves so that the isolation valve for a given filter is closed when the air purge valve for that filter is open, and vice versa.

The filtered gas sample is delivered to a thermocouple tee assembly 61 by a pump 62 though a line 63 to prevent the temperature of the gas sample from dropping below the dewpoint of the gas. The pump is preferably heated and insulated to minimize heat loss. The pump can be heated by any suitable means such as an electrical resistance heating tape wrapped about it. The sample also passes through an in-line heater 64, with an associated temperature controller 65 and sensor/indicators 66, 67. Sensor 66 monitors the temperature of the gas in the flue duct, sensor 67 monitors the temperature of the gas delivered to the thermocouple tee assembly, and controller 65 maintains the gas delivered to the tee assembly at the temperature of the gas in the flue duct.

A flow controller 68 controls the rate at which the gas sample is passed to the heater and the tee assembly.

The tee assembly is enclosed within a temperature controlled cabinet 69 and is maintained at a temperature close to the wet bulb temperature of the gas in order to minimize heat loss. The temperature within the cabinet is maintained at the desired level by means of a heater 71 with an associated temperature sensor 72 and controller 73.

The tee assembly includes a T-shaped vessel 74 having an upper arm 76, a lower arm 77 and a pair of horizontally extending arms 78, 79. The gas sample is introduced into the vessel through arm 78 and exhausted through arm 79. A thermocouple sensor 81 is inserted into the gas stream within the vessel through the upper arm 76, and is surrounded by a liquid absorbent wick 82. The thermocouple is encased in a corrosion resistant metal sheath of a material such as Hastelloy X. The lower portion of the wick extends into a reservoir 83 which is slidably mounted in the lower arm of the T-shaped vessel, with a seal 84 between the reservoir and the arm. A second reservoir 86 is formed in the space between the inner wall of the arm and the outer wall of the reservoir. A water inlet 87 is provided at the lower end of the inner reservoir, and a water outlet or drain 88 is provided in the outer wall of the outer reservoir.

Reservoir 83 is open at the top, and the water from inlet 87 overflows this reservoir and fills reservoir 86, overflowing from it through outlet 88.

The gas sample from the thermocouple assembly is returned to the flue duct through lines 89, 91 and a water trap 92 which removes any condensed moisture from the gas. The water from drain outlet 88 is also discharged through the water trap. Returning the sample gas to the gas duct maintains the static pressure in the tee assembly at approximately the same pressure as the gas in the duct, and this serves to further insure that the conditions of the sample gas closely match those of the gas in the duct. Routing the water from the reservoir drain to the water trap equalizes the pressures in the sample line and the drain line, resulting in a more stable water lever in the tee assembly.

Heated fresh water is continuously supplied to the reservoirs and wick through a filter 93, a pressure control valve 94, a flow controller 96, and a heater 97 with an associated temperature sensor 98 and controller 99. The water supplied to the wick is thus maintained at a temperature close to the wet bulb temperature to prevent heat losses which might otherwise occur.

This system provides close control over the rate at which the water is fed to the wick, the distance the water must travel up the wick, and the temperature of the water. Too much water or too short a distance will flood the wick and produce a temperature reading representative of the water temperature rather than the wet bulb temperature of the gas. Conversely, if too little water flows to the wick or the distance between the thermocouple and the water in the reservoir is too great, the wick will dry out, resulting in erroneously high wet bulb readings.

The entire system with the exception of controllers 59, 65 and sensor 66, is mounted in a temperature controlled cabinet 101 and maintained at a temperature close to the wet bulb temperature to further minimize heat loss. The portion of gas return line 91 outside cabinet 101 is heated by suitable means such as electrical resistance heating tape.

Operation of the system is best understood with reference to the simplified psychometric chart of FIG. 4. Point A represents the temperature and humidity of the flue gas in the gas duct. The wet bulb temperature can be found by following the psychometric line (which for flue gases is essentially equal to the adiabatic saturation line) to point C. At this point, the flue gas is saturated with water and the wet bulb temperature has been reached.

Accurate wet bulb temperatures can only be measured, however, if the decrease in temperature is due solely to the evaporation of water. Heat losses due to other sources (e.g., radiation) will lower the temperature along the constant humidity line, i.e., the line between points A and B in FIG. 4. Following the psychometric line from point B to the saturation line would give a wet bulb temperature at point D, which would be a significant error. If the gas is allowed to cool enough (without a change in the moisture content), the saturation line will now be reached at point E, which represents the dewpoint of the flue gas. This point is often confused with the wet bulb temperature.

The monitoring system of the invention allows the sample gas stream to cool along the line A-B, but the sample is not allowed to reach the dewpoint (point E) where moisture could condense from the gas and result in a decrease in humidity. Instead, the gas is kept above the dewpoint by the heated lines and then reheated back to the temperature at point A, whereby the sample is returned to the same conditions which exist in the duct. Now, the true wet bulb temperature can be measured following the psychometric line from point A to point C.

The invention allows the wet bulb temperature measurement to be made outside the gas duct, which in spray drying systems has tremendous advantages. It also means that the monitor can be located away from the inlet duct, which is often remote, and close to other analyzers (e.g., $SO_2$, $O_2$, opacity, etc.), which is an important advantage from the standpoint of maintenance and calibration.

It is apparent from the foregoing that a new and improved system and method for monitoring the wet bulb temperature in a flue gas stream have been provided. While only certain presently preferred embodiments have been described in detail, as will be apparent to those familiar with the art, certain changes and modifications can be made without departing from the scope of the invention as defined by the following claims.

We claim:

1. In a system for monitoring wet bulb temperature in a flue gas stream: means for extracting a sample of the gas from the flue, means for heating the sample to maintain the sample at substantially the same temperature as the gas in the flue, a sensor for measuring the wet bulb temperature of the sample, a reservoir of liquid, a liquid absorbent wick surrounding the sensor and extending into the liquid in the reservoir, and means for maintaining the liquid in the reservoir at a substantially constant level.

2. The system of claim 1 including means for adjusting the distance between the sensor and the level of the liquid in the reservoir.

3. The system of claim 1 including means for circulating the liquid through the reservoir.

4. The system of claim 1 wherein the means for extracting a sample includes a pair of filters, means for selectively passing the sample through one of the filters, and means for purging the other filter with air to remove particulate matter from its filter surface.

5. In a method of monitoring the wet bulb temperature of a flue gas stream, the steps of: extracting a sample of the gas from the flue, heating the sample to maintain the sample at substantially the same temperature as the gas in the flue, measuring the wet bulb temperature of the sample with a sensor surrounded by a liquid absorbent wick, applying liquid to the wick from a reservoir, and maintaining the liquid in the reservoir at a substantially constant level 6. In a system for monitoring the wet bulb temperature of a gas in a flue: means for extracting a sample of the gas from the flue, means for maintaining the sample above the dewpoint to maintain substantially the same moisture content in the sample as in the gas in the blue, means for heating the sample back to the temperature of the gas in the flue, and a sensor for measuring the wet bulb temperature of the sample when the sample has substantially the same moisture content and temperature as the gas in the flue.

7. In a method of monitoring the wet bulb temperature of a gas in a flue, the steps of: extracting a sample of the gas from the flue, maintaining the sample above the dewpoint to maintain substantially the same moisture content in the sample as in the gas in the flue, heating the sample back to the temperature of the gas in the flue, and measuring the wet bulb temperature of the sample when the sample has substantially the same moisture content and temperature as the gas in the flue.

8. In a system for monitoring wet bulb temperature in a flue gas stream: means for extracting a sample of the gas from the flue, means for heating the sample to maintain the sample at substantially the same temperature as the gas in the flue, a sensor for measuring the wet bulb temperature of the sample, a first reservoir, a liquid absorbent wick surrounding the sensor and extending into the first reservoir, means for introducing a liquid into the lower portion of the first reservoir and allowing it to overflow from the upper portion of said reservoir, a second reservoir positioned to receive the liquid which overflows from the first reservoir, and an overflow drain in the second reservoir for maintaining the liquid at a predetermined level in the second reservoir.

9. The system of claim 8 wherein the first reservoir is positioned concentrically within the second reservoir.

10. The system of claim 9 wherein the position of the first reservoir can be adjusted vertically within the second reservoir.

11. The system of claim 8 including means for heating the liquid introduced into the first reservoir to a temperature substantially equal to the wet bulb temperature of the gas.

12. In a system for monitoring the wet bulb temperature of a gas in a flue: means for extracting a sample of the gas from the flue, means for maintaining the sample at substantially the same temperature and moisture content as the gas in the flue, and means for monitoring the wet bulb temperature of the sample when the sample has substantially the same moisture content and temperature as the gas in the flue.

13. In a method of monitoring the wet bulb temperature of a gas in a flue, the steps of: extracting a sample of the gas from the flue, maintaining the sample at substantially the same temperature and moisture content as the gas in the flue, and monitoring the wet bulb temperature of the sample when the sample has substantially the same moisture content and temperature as the gas in the flue.

* * * * *